United States Patent [19]

Martin et al.

[11] Patent Number: 4,903,726
[45] Date of Patent: Feb. 27, 1990

[54] MEDICAL VACUUM REGULATING CARTRIDGE

[75] Inventors: Gordon D. Martin, Palatine, Ill.; Douglas D. Carden, Barneveld, Wis.; Colin Hodge, Columbia, Md.

[73] Assignees: Aeros Instruments, Inc., Northbrook, Ill.; The BOC Group, Inc., Ohmeda Division, Columbia, Md.

[21] Appl. No.: 83,571

[22] Filed: Aug. 10, 1987

[51] Int. Cl.$^4$ ............................................. G05D 16/06
[52] U.S. Cl. .............................. 137/505.13; 137/495; 137/505.29; 137/505.38; 137/907
[58] Field of Search .......... 92/85 A; 137/495, 505.13, 137/505.29, 505.38, 907; 251/284; 604/119

[56] References Cited

U.S. PATENT DOCUMENTS

| | | |
|---|---|---|
| 1,620,322 | 3/1927 | Browne . |
| 4,137,912 | 2/1979 | O'Neil . |
| 4,238,991 | 12/1980 | Pickles . |
| 4,513,785 | 4/1985 | Kenny . |

Primary Examiner—Gerald A. Michalsky
Attorney, Agent, or Firm—Potthast & Ring

[57] ABSTRACT

A vacuum regulating cartridge (10) having a roller diaphragm (52), a coil spring (54) and a cantilevered spring arm (68) to form a regulation system for regulating vacuum in a medical regulating vacuum controller (26).

26 Claims, 2 Drawing Sheets

MEDICAL VACUUM REGULATING CARTRIDGE

BACKGROUND OF THE INVENTION

This invention relates to a vacuum regulating cartridge used to regulate vacuum pressure of a medical regulating vacuum controller used to control the application of vacuum pressure used to draw bodily fluids from a patient.

In various medical applications vacuum pressure controllers are employed to control the level of vacuum pressure applied to draw bodily fluids from a patient. Such controllers have a housing within which is contained a vacuum pressure meter, an inlet port for connection with a supply of vacuum pressure, a non-regulated or line vacuum chamber in open communication with the inlet port, a regulation vacuum chamber with a valve opening for controlled communication with the line vacuum chamber and an outlet port for connection of regulated vacuum pressure to the patient.

The vacuum regulation chamber includes a well within which is slideably received a vacuum regulating cartridge. The cartridge carries a movably mounted valve head for mating engagement with a valve seat of the valve opening. The carriage body is mounted for sliding movement in response to rotation of a knob to selectively move the valve head to different positions relative to the valve seat. These different positions correspond to different vacuum levels selected from a range of different vacuum pressures.

In known cartridges, the cartridge body contains a bellows-like apparatus which responds to decreases in pressure in the well to move the valve head closer to the valve opening to decrease the effective valve opening and thereby increase the pressure in the well. Likewise, when the vacuum decreases in the well, the bellows respond by moving the valve head away from the valve seat to increase the vacuum. In this way the vacuum which appears at the output port and provided to the patient is regulated relative to the line vacuum.

While the bellows-like apparatus performs its function of automatically moving the valve head for purposes of regulation, it suffers from several disadvantages. Because of the complexity of the bellows-like structure, it is both relatively expensive and difficult to maintain tolerances with respect to the degree of responsive movement for a given change in vacuum pressure. In addition, it has been difficult to reliably obtain the degree of control and regulation over the wider range of control from (0-500 mm Hg vs. 0-200 mm Hg) as is now sometimes required for various applications when using the known bellows-type cartridges.

SUMMARY OF THE INVENTION

Accordingly, the principal object of the present invention is to provide an improved regulating cartridge in which the disadvantages of the known bellows-type cartridges have been eliminated.

In a preferred embodiment, this is achieved through provision of a vacuum regulating cartridge with an improved regulating mechanism for controlling movement of the valve head comprising, among other things, a flexible diaphragm mounted within the body of the cartridge to define a relatively air tight movable wall of the vacuum regulation chamber, means for linking the valve head to the flexible diaphragm to cause the valve head to move away from the body in response to regulation chamber volume reducing movement of the flexible diaphragm and a spring resiliently opposing movement of the valve head away from the body. Preferably, another spring resists movement of the valve head toward the body at low levels of vacuum in the vacuum regulation chamber.

In another embodiment, the regulating mechanism comprises a resilient diaphragm mounted within the body to define a relatively air tight movable wall of the vacuum regulation chamber in a forward part of the body, means for linking the valve head to the membrane to cause the valve head to move rearwardly toward the body with rearward movements of membrane, and a spring carried by the diaphragm within the body but outside of the vacuum regulation chamber for resiliently resisting rearward movement of the diaphragm at relatively low pressures.

BRIEF DESCRIPTION OF THE DRAWINGS

The foregoing objects, features and advantages will be described in greater detail and other advantageous features will be made apparent from the following detailed description of the preferred embodiments given in reference to the figures of the drawing, in which.

DETAILED DESCRIPTION

Figure 1:
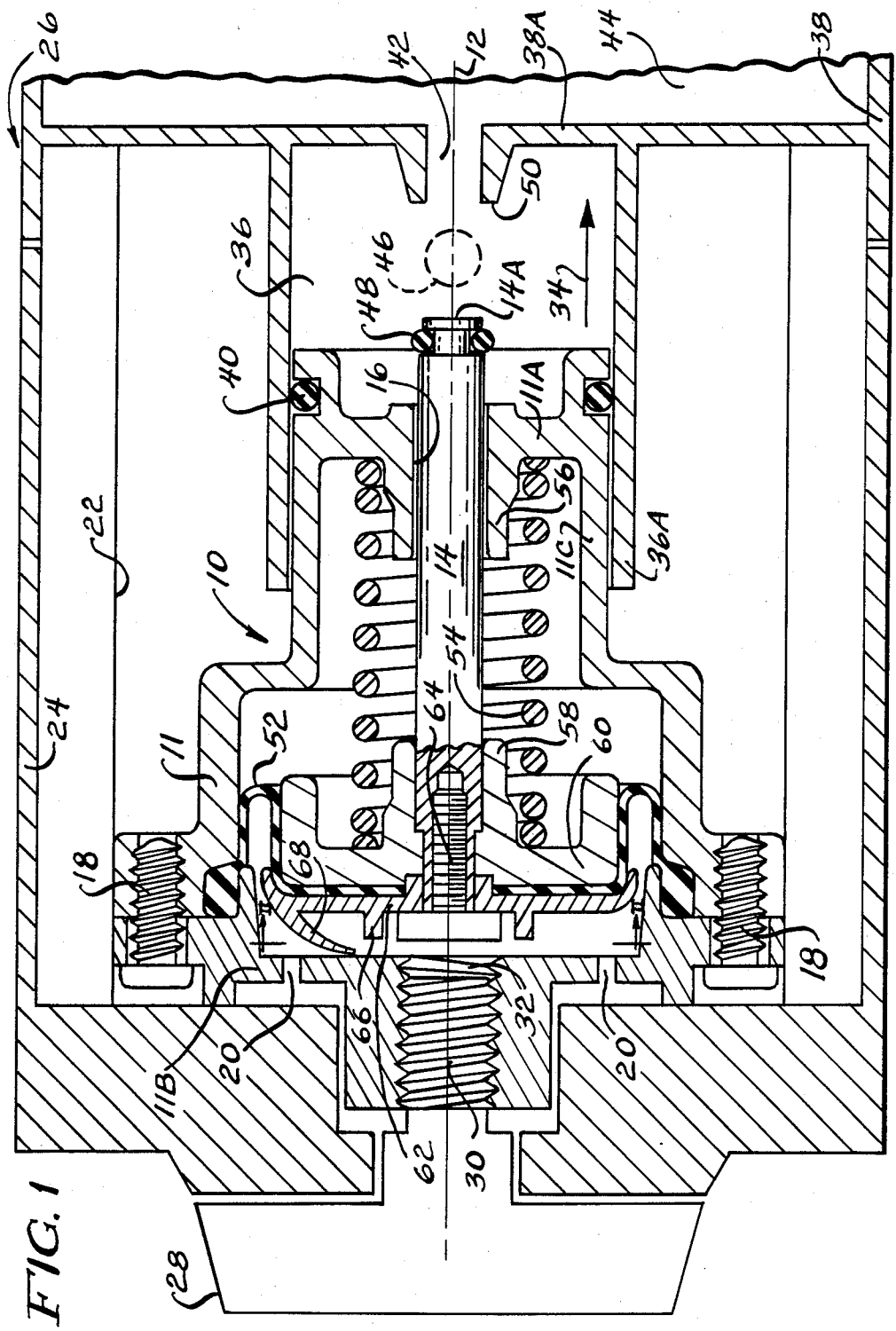
FIG. 1 is an enlarged cross-sectional side view of the preferred embodiment of the vacuum regulating cartridge of the present invention.

Referring now to FIG. 1, the preferred embodiment of the vacuum regulating cartridge is seen to include a number of known parts which cooperate with other known parts of regulating vacuum controllers as discussed in the background, above.

Briefly, the cartridge 10 has an elongated bellows-plastic body 11 which is symmetrical about the center axis 12 within which is contained part of a valve stem 14 mounted for sliding movement within a valve stem opening 16 in a front end wall 11A of cartridge body 11. The rear end wall 11B of body 11 is secured to the remainder of body 11 by a pair of screws 18 and has a pair of air holes 20 for opening the rearward portion of the cartridge to atmospheric pressure.

The entire cartridge body is mounted to slide within a channel 22 of the cover 24 of the controller 26 in response to rotation of a knob 28 attached to an adjustment screw 30 which fits into a threaded screw hole 32 at the rear end wall 11B. As the knob 28 is rotated clockwise, the screw hole 32 is drawn down onto the adjustment screw 30 and the cartridge 10 slides rearwardly in a direction opposite to that of arrow 34 to increase vacuum. When it is rotated counterclockwise, the rear end wall 11B moves off the adjustment screw in the direction of arrow 34 to reduce vacuum. As seen in FIG. 1, the adjustment screw has been adjusted for maximum vacuum.

A narrowed forward section 11C of the body 11 is snuggly received within a well 36 of the base 38 of the controller 26. An O-ring seal 40 prevents the entry of air into the well in the gap between the sides 36A of the well 36 and the narrowed forward section 11C of cartridge body 11, while a valve hole 42 in the base of well 38A provides communication between the well and unregulated line vacuum in a line vacuum chamber 44. The well also has communication with a patient outlet port 46 as schematically illustrated in broken line.

At the distal end 14A of valve stem 14 is another O-ring 48 mounted in a channel for mating engagement with a valve seat 50 surrounding valve opening 42. When the selection knob 28 is rotated counterclockwise until the O-ring 48 presses against the valve seat 50 and the distal end 14A enters valve opening 42, the vacuum is off and the regulation chamber bleeds to atmospheric pressure. However, as the knob 28 is rotated clockwise, the O-ring is caused to move away from the valve seat 50 to increase the average amount of vacuum in the well. As explained below, the location of the O-ring seal 48 is closer to the valve seat 50 when vacuum is being provided in the line, as opposed to that shown in FIG. 1 in which the unit is off and no line vacuum present.

Unlike known regulating cartridges, in the regulating cartridge of the present invention, the automatic movement of the valve head 48 in response to fluctuations of line vacuum to achieve regulation is achieved through means including an air impervious flexible diaphragm 52. The flexible diaphragm 52 seals the forward section 11C of the cartridge body 11 against atmospheric pressure at air holes 20 at the rear end wall 11B. Leakage between the well 36 and forward portion 11C creates a single regulation chamber which is partly defined by the moving wall of diaphragm 52.

The diaphragm 52 functions to regulate the vacuum in the regulation chamber by moving to increase or decrease its volume and thereby increase or decrease the vacuum. When the vacuum in the regulation chamber increases due to a surge in line vacuum, the diaphragm 52 is caused to move forwardly in the direction of arrow 34. This decreases the effective volume of the regulation chamber and thereby absorbs or reduce the amount of the vacuum surge, so it is not felt by the patient at the patient outlet. Likewise, if there is a sudden decrease in vacuum, the diaphragm 52 will move in a direction opposite to that of arrow 34 to increase the effective volume of the regulation chamber and thereby increase the vacuum.

In addition to changing the volume, the movement of the diaphragm 52 causes movement of the valve head 48 to move either closer or farther away from the valve seat 50 to achieve regulation of the valve opening as appropriate to regulate the vacuum in the regulation chamber. When the diaphragm 52 moves forward to reduce the vacuum by volume reduction, the valve head 48 is also moved forward to increase the seal of the valve opening 42. Likewise, when the diaphragm 52 moves in a direction to increase the volume and the vacuum, it also causes the valve head, or O-ring seal, to move away from the valve opening 42 to increase the communication to line vacuum.

Preferably, a rolling diaphragm is employed as diaphragm 52 and a coil spring 54 is used to resiliently resist movement of the diaphragm 52 in the volume decreasing forward direction of arrow 34. The coil spring 54 is wound about stem 14 to axially align the force. The coil spring is also kept aligned by means of a boss 56 at the forward end wall 11A and another boss 58 projecting from a piston 60. The piston boss 58 has a mounting hole within which is received the one end of the valve stem 14 to make a linkage between O-ring seal 48 and the diaphragm 52.

On the atmospheric side of diaphragm 52, a retainer 62 is secured to the diaphragm to sandwich it between one side of the retainer 62 and a flat side of the piston 60. This tends to stiffen the diaphragm and makes it more resistant to movement toward the valve opening 42. A single screw fastener 64 holds together all of the retainer 62, the diaphragm 52, the piston 60 and the valve stem 14.

Figure 2:
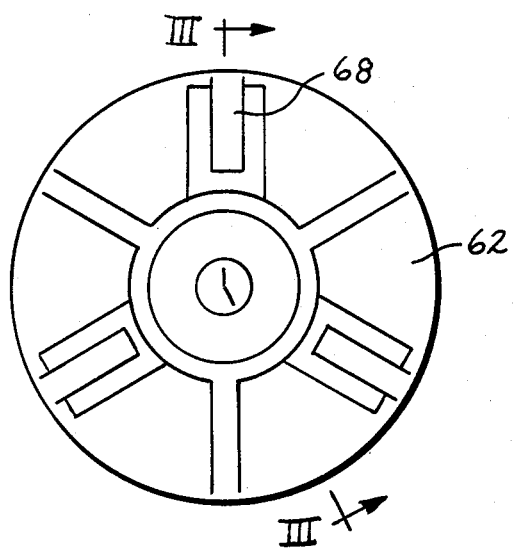
FIG. 2 is an enlarged plan view of a low pressure retainer spring as seen from section line II—II of FIG. 1.
Figure 3:
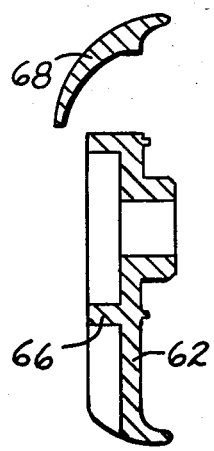
FIG. 3 is an enlarged sectional view of the retainer spring taken along section line III—III of FIG. 2.

The retainer 62, in addition to strengthening and securing the diaphragm 52, carries a plurality of relatively rigid arms 66 engageable with the rear end wall 11B to resist rearward movement and a plurality of cantilevered spring arms 68 which resiliently press against the rear end wall to resiliently resist volume increasing movement of the diaphram 52 at low vacuum levels, as also seen in FIGS. 2 and 3.

While a particular embodiment has been described, it should be appreciated that many variations may be made without departing from the scope of the appended claims which define the invention. For instance, while special springs are shown, other types of springs could also be successfully employed. Also, a resilient diaphragm which tends to return to its home position could be employed to assist the springs or possibly even to be used in lieu of springs.

We claim:

1. In a medical vacuum regulating cartridge having a hollow body slideably connected with a well to form at least a part of a vacuum regulation chamber said well having a patient outlet port for provision of regulated vacuum pressure and an inlet supply port connectable with a supply of unregulated vacuum pressure, and a valve head mounted to the body for movement into and out of engagement with the inlet supply port of said well, the improvement being a regulating mechanism for controlling the movement of the valve head to regulate the pressure within the vacuum regulation chamber, comprising:

a flexible diaphragm mounted within the body to define a relatively air tight movable wall of the vacuum regulation chamber, said wall moving to reduce the volume of the regulation chamber in response to decreases in pressure therein;

means for linking the valve head outside the body to the flexible diaphragm within the body to cause the valve head to move away from the body and into tighter engagement with the outlet port in response to regulation chamber volume reducing movements of the flexible diaphragm; and a spring within the body resiliently opposing movement of the valve head away from the body and into tighter engagement with the outlet port.

2. The vacuum regulating cartridge of claim 1 in which said linking means comprises an elongate valve stem mounted to the diaphragm at one end thereof within the cartridge body and having a portion extending through the body and a wall at an opposite end of the cartridge body to carry the valve head at the outside of the body, and said spring comprises a coil spring engaged with the diaphragm and wound around the portion of the valve stem extending through the cartridge body.

3. The vacuum regulating cartridge of claim 1 including another spring located within the body but without the regulation chamber for resisting movement of the diaphragm in a direction to increase the volume of the regulation chamber.

4. The vacuum regulating cartridge of claim 3 in which said other spring is substantially smaller than the spring within the vacuum regulation chamber.

5. The volume regulating cartridge of claim 1 in which said linking means includes
   a piston,
   means for securing the piston to the diaphragm,
   an elongate valve stem for carrying the valve head at a distal end thereof, and
   means for securing an opposite end of the valve stem to the piston.

6. The vacuum regulating cartridge of claim 5 in which said linking means includes a single fastener for fastening together all of the diaphragm, piston and stem.

7. The volume regulating cartridge of claim 5 in which said securing means includes a retainer and means for fastening together the retainer, diaphragm and piston in that order.

8. The vacuum regulating cartridge of claim 1 in which said diaphragm is a resilient roller diaphragm.

9. In a vacuum regulating cartridge having a body with a vacuum regulation chamber connectable with a supply of vacuum pressure and a valve head mounted to the body for movement relative thereto, the improvement being a regulating mechanism for controlling the movement of the valve head, comprising:
   a flexible diaphragm mounted within the body to define a relatively air tight movable wall of the vacuum regulation chamber, said wall moving to reduce the volume of the regulation chamber in response to decreases in pressure therein;
   means for linking the valve head to the flexible diaphragm to cause the valve head to move away from the body in response to regulation chamber volume reducing movements of the flexible diaphragm;
   a spring resiliently opposing movement of the valve head away from the body; and
   means for resisting movement of the diaphragm in a direction to increase the volume of the regulation chamber at only relatively high pressure levels in the vacuum regulation chamber.

10. The vacuum regulating cartridge of claim 9 including another means for resiliently resisting movement of the diaphragm in a direction to increase the volume of the regulation chamber at relatively low pressure levels in the vacuum regulation chamber.

11. The vacuum regulating cartridge of claim 10 in which
   said diaphragm is resilient and predisposed to move in a direction to oppose the spring to move the valve head toward the body, and
   the resilient movement resisting means includes the resiliency of said diaphragm itself.

12. The vacuum regulating cartridge of claim 11 including a relatively rigid retainer secured to a portion of the diaphragm to reduce its resiliency and increase its resistance to movement in a direction to increase the volume of the regulation chamber at relatively high pressure levels therein.

13. The vacuum regulating cartridge of claim 12 in which
   said cartridge body has an end wall opposite the vacuum regulation chamber, and
   said retainer includes legs for abutting the end wall to assist in resisting movement of the diaphragm to increase the volume of the regulation chamber.

14. The vacuum regulating cartridge of claim 9 in which said movement resisting means includes
   an end wall opposite the vacuum regulation chamber, and
   a retainer attached to the diaphragm with at least one leg for abutting against said end wall.

15. The vacuum regulating cartridge of claim 9 in which said movement resisting means includes a spring.

16. In a vacuum regulating cartridge having a body with a vacuum regulation chamber connectable with a supply of vacuum pressure and a valve head mounted to the body for movement relative thereto, the improvement being a regulating mechanism for controlling the movement of the valve head, comprising:
   a flexible diaphragm mounted within the body to define a relatively air tight movable wall of the vacuum regulation chamber, said wall moving to reduce the volume of the regulation chamber in response to decreases in pressure therein;
   means for linking the valve head to the flexible diaphragm to cause the valve head to move away from the body in response to regulation chamber volume reducing movements of the flexible diaphragm;
   a spring resiliently opposing movement of the valve head away from the body:
   means for resisting movement of the diaphragm in a direction to increase the volume of the regulation chamber at relatively high pressure levels in the vacuum regulation chamber including
   an end wall opposite the vacuum regulation chamber, and
   a retainer attached to the diaphragm with at least one leg for abutting against said end wall said at least one leg including a flexible spring for resiliently resisting said movement.

17. In a vacuum regulating cartridge having a body with a vacuum regulation chamber connectable with a supply of vacuum pressure and a valve head mounted to the body for movement relative thereto, the improvement being a regulating mechanism for controlling the movement of the valve head, comprising:
   a flexible diaphragm mounted within the body to define a relatively air tight movable wall of the vacuum regulation chamber, said wall moving to reduce the volume of the regulation chamber in response to decreases in pressure therein;
   means for linking the valve head to the flexible diaphragm to cause the valve head to move away from the body in response to regulation chamber volume reducing movements of the flexible diaphragm;
   a spring resiliently opposing movement of the valve head away from the body; and
   means for resisting movement of the diaphragm in a direction to increase the volume of the regulation chamber at relatively high pressure levels in the vacuum regulation chamber including
   a spring having at least one resilient cantilevered spring arm.

18. In a vacuum regulating cartridge having a body with a vacuum regulation chamber connectable with a supply of vacuum pressure and a valve head mounted to the body for movement relative thereto, the improvement being a regulating mechanism for controlling the movement of the valve head, comprising:
   a flexible diaphragm mounted within the body to define a relatively air tight movable wall of the vacuum regulation chamber, said wall moving to reduce the volume of the regulation chamber in response to decreases in pressure therein;

means for linking the valve head to the flexible diaphragm to cause the valve head to move away from the body in response to regulation chamber volume reducing movements of the flexible diaphragm;

a spring resiliently opposing movement of the valve head away from the body;

another spring located within the body but without the regulation chamber for resisting movement of the diaphragm in a direction to increase the volume of the regulation chamber including a spring retainer with a base attached to the diaphragm within the body but outside of the vacuum regulation chamber, and a plurality of cantilevered spring arms extending away from the vacuum regulation chamber for resilient engagement with a back portion of the body to resist volume increasing movement of the diaphragm.

19. The vacuum regulating cartridge of claim 18 in which said spring arms are integrally molded together with the base of the retainer.

20. In a vacuum regulating cartridge having a body with a vacuum regulation chamber connectable with a supply of vacuum pressure and a valve head mounted to the body for movement relative thereto, the improvement being a regulating mechanism for controlling the movement of the valve head, comprising:

a flexible diaphragm mounted within the body to define a relatively air tight movable wall of the vacuum regulation chamber, said wall moving to reduce the volume of the regulation chamber in response to decreases in pressure therein;

means for linking the valve head to the flexible diaphragm to cause the valve head to move away from the body in response to regulation chamber volume reducing movements of the flexible diaphragm including a piston, means for securing the piston to the diaphragm including a retainer, and means for fastening together the retainer, diaphragm and piston in that order, an elongate valve stem for carrying the valve seat at a distal end thereof, and means for securing an opposite end of the valve stem to the piston including a retainer carrying a spring to resist movement of the diaphragm in a direction away from the valve stem at relatively higher pressures; and a spring resiliently opposing movement of the valve head away from the body.

21. In a vacuum regulating cartridge having a body with a vacuum regulation chamber connectable with a supply of vacuum pressure and a valve head mounted to the body for movement relative thereto, the improvement being a regulating mechanism for controlling the movement of the valve head, comprising:

a resilient diaphragm mounted within the body to define a relatively air tight movable wall of the vacuum regulation chamber in a forward part of the body;

means for linking the valve head to the membrane to cause the valve head to move rearwardly toward the body with rearward movements of membrane; and a spring carried by the diaphragm within the body but outside of the vacuum regulation chamber for resiliently resisting forward movement of the diaphragm at relatively higher pressures.

22. The vacuum regulating cartridge of claim 21 in which said body includes a rearward wall against which bears said spring only at relatively higher pressures.

23. The vacuum regulating cartridge of claim 21 including another spring within the vacuum regulation chamber for resisting forward movement of the diaphragm.

24. In a vacuum regulating cartridge having a body with a vacuum regulation chamber connectable with a supply of vacuum pressure and a valve head mounted to the body for movement relative thereto, the improvement being a regulating mechanism for controlling the movement of the valve head, comprising:

a resilient diaphragm mounted within the body to define a relatively air tight movable wall of the vacuum regulation chambers in a forward part of the body;

means for linking the valve head to the membrane to cause the valve head to move rearwardly toward the body with rearward movements of the diaphragm;

a spring carried by the diaphragm within the body but outside of the vacuum regulation chamber for resiliently resisting forward movement of the diaphragm at relatively higher pressures; and a leg carried by the diaphragm to engage a rearward wall of the body to block excessive rearward movement of the diaphragm.

25. The vacuum regulating cartridge of claim 24 in which said spring engages the rearward wall to resiliently resist rearward movement of the diaphragm before engagement therewith by the leg to block movement.

26. In a vacuum regulating cartridge having a body with a vacuum regulation chamber connectable with a supply of vacuum pressure and a valve head mounted to the body for movement relative thereto, the improvement being a regulating mechanism for controlling the movement of the valve head, comprising:

a resilient diaphragm mounted within the body to define a relatively air tight movable wall of the vacuum regulation chamber in a forward part of the body;

means for linking the valve head to the membrane to cause the valve head to move rearwardly toward the body with rearward movements of membrane; and a spring carried by the diaphragm within the body but outside of the vacuum regulation chamber for resiliently resisting forward movement of the diaphragm at relatively higher pressures including a plurality of cantilevered spring arms.

* * * * *